United States Patent
Tomaki et al.

(10) Patent No.: US 12,319,635 B2
(45) Date of Patent: Jun. 3, 2025

(54) METHOD FOR PRODUCING AROMATIC AMINOMETHYL

(71) Applicant: MITSUBISHI GAS CHEMICAL COMPANY, INC., Chiyoda-ku (JP)

(72) Inventors: Keisuke Tomaki, Kanagawa (JP); Shinyou Shirai, Okayama (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 345 days.

(21) Appl. No.: 18/004,261

(22) PCT Filed: Jul. 6, 2021

(86) PCT No.: PCT/JP2021/025396
§ 371 (c)(1),
(2) Date: Jan. 4, 2023

(87) PCT Pub. No.: WO2022/019105
PCT Pub. Date: Jan. 27, 2022

(65) Prior Publication Data
US 2023/0265042 A1   Aug. 24, 2023

(30) Foreign Application Priority Data
Jul. 22, 2020 (JP) .................... 2020-125155

(51) Int. Cl.
C07C 209/48   (2006.01)
C07C 209/84   (2006.01)

(52) U.S. Cl.
CPC .......... *C07C 209/48* (2013.01); *C07C 209/84* (2013.01)

(58) Field of Classification Search
None
See application file for complete search history.

(56) References Cited

U.S. PATENT DOCUMENTS

| 6,080,884 A | 6/2000 | Ziemecki et al. |
| 2004/0002614 A1 | 1/2004 | Amakawa et al. |
| 2005/0054886 A1* | 3/2005 | Jones ............. C07C 29/09 |
| | | 568/812 |
| 2008/0154061 A1 | 6/2008 | Ernst et al. |
| 2008/0214871 A1 | 9/2008 | Ernst et al. |
| 2008/0293951 A1 | 11/2008 | Iwvama et al. |

FOREIGN PATENT DOCUMENTS

| JP | 54-41804 A | 4/1979 |
| JP | 2002-205980 A | 7/2003 |
| JP | 2004-35427 A | 2/2004 |
| JP | 2008-528459 A | 7/2008 |
| JP | 2008-531521 A | 8/2008 |
| WO | WO 2007/023788 A1 | 3/2007 |

OTHER PUBLICATIONS

International Search Report issued Sep. 7, 2021 in PCT/JP2021/025396, filed on Jul. 6, 2021, 3 pages.

* cited by examiner

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for producing an aromatic aminomethyl, comprising hydrogenating an aromatic nitrile in an organic solvent comprising a polar organic solvent having a solubility parameter (SP value) of 9 or more in the presence of a quaternary ammonium compound, at least one metal hydroxide selected from the group consisting of an alkali metal hydroxide and an alkaline earth metal hydroxide, and a hydrogenation catalyst.

18 Claims, No Drawings

METHOD FOR PRODUCING AROMATIC AMINOMETHYL

CROSS-REFERENCE TO RELATED APPLICATIONS

The present application is a 35 U.S.C. § 371 national stage patent application of International patent application PCT/JP2021/025396, filed on Jul. 6, 2021, which is based on and claims the benefits of priority to Japanese Application No. 2020-125155, filed on Jul. 22, 2020. The entire contents of these applications are incorporated herein by reference.

TECHNICAL FIELD

The present invention relates to a method for producing an aromatic aminomethyl by hydrogenating an aromatic nitrile.

BACKGROUND ART

An aromatic aminomethyl is useful as a starting material or an intermediate for drugs, agricultural chemicals, resins, curing agents, etc. In particular, xylenediamine having two aminomethyl groups is a very useful compound as a starting material for a polyamide resin, a curing agent or the like, or an intermediate for an isocyanate.

As a method for producing an aromatic aminomethyl, a method in which an aromatic nitrile is hydrogenated is carried out.

In the hydrogenation of the aromatic nitrile, a technique using liquid ammonia as a solvent is known. From the environmental consideration, however, liquid ammonia needs to be recovered without releasing it to the outside after the hydrogenation reaction, so that the production load is heavy, and regarding a production method without using liquid ammonia, various studies have been made.

For example, in Patent Literature 1, a method for producing an aromatic cyanoaminomethyl, in which an aromatic nitrile is hydrogenated using a palladium catalyst in the presence of an alcohol and a tetraalkylammonium hydroxide, is disclosed for the purpose of obtaining an aromatic cyanoaminomethyl that is one of aromatic aminomethyls in a high yield under mild reaction conditions and by simple reaction operations without using liquid ammonia while suppressing the by-production of an aromatic diaminomethyl.

CITATION LIST

Patent Literature

PTL1: JP 2002-205980 A

SUMMARY OF INVENTION

Technical Problem

In order to use an aromatic aminomethyl as a starting material for a polyamide resin, a curing agent or the like, or an intermediate for an isocyanate, an aromatic aminomethyl of extremely high purity has been desired, and in the production method without using liquid ammonia, a method for obtaining an aromatic aminomethyl in a high yield has been desired.

According to the method of Patent Literature 1, hydrogenation can be carried out under mild reaction conditions without using liquid ammonia, but a problem is that impurities are contained in the resulting aromatic aminomethyl. If impurities are contained, they inhibit polymerization when the aromatic aminomethyl is used as a starting material for a polyamide resin or the like, as described above.

On that account, a synthesis method that gives a high yield and is capable of suppressing formation of impurities has been desired.

Then, an object of the present invention is to provide a production method by which an aromatic aminomethyl can be obtained in a high yield without substantially using liquid ammonia, and formation of impurities can also be suppressed.

Solution to Problem

The present inventors have earnestly studies, and as a result, they have found that the above object can be achieved by carrying out hydrogenation of an aromatic nitrile in a specific solvent in the presence of a quaternary ammonium compound and a specific metal hydroxide.

That is to say, the present invention is a method for producing an aromatic aminomethyl, comprising hydrogenating an aromatic nitrile in an organic solvent comprising a polar organic solvent having a solubility parameter (SP value) of 9 or more in the presence of a quaternary ammonium compound, at least one metal hydroxide selected from the group consisting of an alkali metal hydroxide and an alkaline earth metal hydroxide, and a hydrogenation catalyst.

Advantageous Effects of Invention

According to the production method of the present invention, an aromatic aminomethyl can be obtained in a high yield without substantially using liquid ammonia, and formation of impurities can also be inhibited.

DESCRIPTION OF EMBODIMENTS

The method for producing an aromatic aminomethyl of the present invention comprises hydrogenating an aromatic nitrile in an organic solvent comprising a polar organic solvent having a solubility parameter (SP value) of 9 or more in the presence of a quaternary ammonium compound, at least one metal hydroxide selected from the group consisting of an alkali metal hydroxide and an alkaline earth metal hydroxide, and a hydrogenation catalyst.

The production method of the present invention will be described in detail hereinafter.

[Organic Solvent]

The organic solvent used in the present invention comprises a polar organic solvent having a solubility parameter (SP value) of 9 or more.

It is thought that by using a polar organic solvent having a SP value of 9 or more in the production method of the present invention, an aromatic aminomethyl that is a product is distributed therein, and hydrogenation reaction can be efficiently promoted.

The organic solvent used in the present invention may consist of the above polar organic solvent, but it is thought that by further using a non-polar organic solvent having a SP value of less than 9, the aromatic nitrile and hydrogen that are starting materials are favorably dissolved, and hydrogenation reaction can be efficiently carried out.

The non-polar organic solvent having a SP value of less than 9 is not particularly limited, but it is preferably a hydrocarbon solvent.

Hereinafter, each solvent will be described.

(Polar Organic Solvent Having Solubility Parameter (SP Value) of 9 or More)

The polar organic solvent used in the present invention has a solubility parameter (SP value) of 9 or more, preferably 10 or more, more preferably 11 or more, still more preferably 12 or more, and still much more preferably 13 or more. The upper limit value is preferably 20 or less, more preferably 17 or less, and still more preferably 15 or less.

The SP value in the present invention is a value determined by the following Hildebrand solubility parameter equation.

$$\text{Solubility parameter (SP value)} = (\Delta H_A^V - RT)^{0.5} / V_A^{0.5}$$

$\Delta H_A^V$: enthalpy of vaporization of liquid A (polar organic solvent)

R: gas constant

T: temperature $V_A$: molar volume of liquid A

The polar organic solvent used in the present invention is one or more selected from the group consisting of an alcohol, an ester, an amide, a sulfoxide, a ketone and an amine, and an alcohol is preferable.

Examples of the alcohols include a monohydric alcohol and a polyhydric alcohol, and a monohydric alcohol is preferable. Examples of the monohydric alcohols include an aliphatic alcohol and an aromatic alcohol, and an aliphatic alcohol is preferable.

From the viewpoint of industrially easy availability, the number of carbon atoms of the aliphatic alcohol is preferably 1 to 8, more preferably 1 to 4, and still more preferably 1 or 2.

Specific examples of the aliphatic alcohols include methanol (SP value 14.5), ethanol (SP value 12.7), n-propanol (SP value 11.9), isopropanol (SP value 11.5), n-butanol (SP value 11.4), sec-butanol (SP value 10.8), tert-butanol (SP value 10.6), pentanol, hexanol (SP value 10.7), heptanol (SP value 10.6), and n-octanol (SP value 10.3), and preferable is one or more selected from the group consisting of methanol, ethanol, n-propanol, isopropanol and n-butanol, more preferable is one or more selected from the group consisting of methanol and ethanol, and still more preferable is methanol.

(Hydrocarbon Solvent)

The organic solvent used in the present invention preferably further comprises a hydrocarbon solvent.

The hydrocarbon solvent is one or more selected from the group consisting of an aromatic hydrocarbon solvent and an aliphatic hydrocarbon solvent, and an aromatic hydrocarbon solvent is preferable.

The solubility parameter (also referred to as SP value hereinafter) of the hydrocarbon solvent is preferably less than 9. The lower limit value is preferably 7.0 or more, and more preferably 8.0 or more. It is thought that when the hydrocarbon solvent is an aromatic hydrocarbon solvent, an aromatic nitrile and hydrogen that are starting materials are favorably dissolved, and hydrogenation reaction can be efficiently carrier out. It is thought that also due to the SP value of less than 9, an aromatic nitrile and hydrogen that are starting materials are favorably dissolved, and hydrogenation reaction can be efficiently carried out.

When the hydrocarbon solvent is an aromatic hydrocarbon solvent, the number of carbon atoms of the aromatic hydrocarbon solvent is preferably 7 to 12, more preferably 7 to 9, and still more preferably 8 to 9.

Specific examples of the aromatic hydrocarbon solvents include monocyclic aromatic hydrocarbon compounds, such as toluene, ethylbenzene, three isomers of xylene (o-xylene, m-xylene, p-xylene), mesitylene and pseudocumene, and polycyclic aromatic hydrocarbon compounds, such as naphthalene and methylnaphthalene, and monocyclic aromatic hydrocarbon compounds are preferable. From the viewpoints of favorable dissolution of the aromatic nitrile and hydrogen that are starting materials and industrially easy availability, particularly xylene and mesitylene are more preferable, xylene (SP value 8.8) is still more preferable, m-xylene and p-xylene are still much more preferable, and m-xylene is still much more preferable.

(Composition of Organic Solvent)

The organic solvent in the present invention refers to the whole of liquid compounds (the whole of liquid organic compounds) contained in the solution in the hydrogenation reaction, except an aromatic nitrile that is a starting material and an aromatic aminomethyl that is a product.

The organic solvent used in the present invention may consist of the polar organic solvent, as previously described, but it is preferable to further use a non-polar organic solvent having a SP value of less than 9. The non-polar organic solvent having a SP value of less than 9 is not particularly limited, but it is preferably a hydrocarbon solvent.

When the organic solvent comprises a hydrocarbon solvent and a polar organic solvent, the mass ratio of the hydrocarbon solvent to the polar organic solvent (hydrocarbon solvent/polar organic solvent) in the organic solvent is preferably 60/40 to 99/1, more preferably 70/30 to 99/1, still more preferably 80/20 to 99/1, and still much more preferably 82/18 to 99/1. By using the hydrocarbon solvent in a larger amount than that of the polar organic solvent, the concentration of the nitrile dissolved in the hydrocarbon solvent is decreased, and a high-boiling point substance is hardly formed on the catalyst.

The total content of the hydrocarbon solvent and the polar organic solvent in the organic solvent is preferably 90 to 100 mass %, more preferably 95 to 100 mass %, and still more preferably 99 to 100 mass %.

The content of water in the organic solvent is preferably 5 mass % or less, more preferably 2 mass % or less, and still more preferably 1 mass % or less. It is thought that by setting the water content to 5 mass % or less, side reaction with the starting material can be inhibited, and the yield of the product can be enhanced. It is preferable that water should not be substantially contained, and the lower limit value may be 0 mass %.

It is preferable that the organic solvent in the present invention should not substantially contain liquid ammonia, and it is more preferable that it should not contain liquid ammonia. Since the liquid ammonia is not contained, the production load imposed on the recovery of ammonia can be reduced.

A difference in the SP value between the hydrocarbon solvent and the polar organic solvent in the organic solvent is preferably 0.5 or more, more preferably 1.0 or more, still more preferably 2.0 or more, and still much more preferably 4.0 or more. The difference is preferably 12 or less, more preferably 10 or less, still more preferably 8 or less, and still much more preferably 6 or less.

A combination of the hydrocarbon solvent and the polar organic solvent in the organic solvent is preferably that of a monocyclic aromatic hydrocarbon compound and an alcohol, more preferably that of xylene and an aliphatic alcohol having 1 or 2 carbon atoms, and still more preferably that of m-xylene and methanol.

(Quaternary Ammonium Compound)

The method for producing an aromatic aminomethyl of the present invention uses, as alkaline compounds, a quaternary ammonium compound, and at least one metal hydroxide selected from the group consisting of an alkali metal hydroxide and an alkaline earth metal hydroxide.

By using the quaternary ammonium compound and the metal hydroxide at the same time, an aromatic aminomethyl can be obtained in a high yield, and formation of impurities can also be suppressed. The reason why an aromatic aminomethyl can be obtained in a high yield and formation of impurities can also be suppressed as just described is not clear, but it is thought as follows.

The quaternary ammonium compound does not bring about corrosion of a reaction container and the like, catalyst deterioration, etc., and is a compound that is essential for stably obtaining an aromatic aminomethyl in a high yield, but it reacts with an aromatic aminomethyl during distillation and forms impurities. It is thought that use of an alkali metal or the like in combination contributes to reduction of impurities, as the hydroxide of an alkali metal or the hydroxide of an alkaline earth metal inhibits the reaction for forming impurities. Moreover, it is thought that the yield is improved while properties of the alkali metal or the alkaline earth metal to cause catalyst deterioration are reduced, as the quaternary ammonium salt preferentially acts on the catalyst in the reaction.

Examples of the quaternary ammonium compounds used in the present invention include a tetraalkylammonium hydroxide and an organic acid tetraalkylammonium salt, and it is preferable to use one or more selected from the group consisting of these, and among these, a tetraalkylammonium hydroxide is more preferable.

Examples of the tetraalkylammonium hydroxides include tetramethylammonium hydroxide, tetraethylammonium hydroxide and tetrabutylammonium hydroxide, and preferable are tetramethylammonium hydroxide and tetraethylammonium hydroxide, and from the viewpoint of suppressing impurities, tetraethylammonium hydroxide is more preferable.

Examples of the organic acid tetraalkylammonium salts include a tetraalkylammonium phenoxide, a fatty acid tetraalkylammonium salt, and a tetraalkylammonium tetraphenylborate.

The fatty acid tetraalkylammonium salt is, for example, tetramethylammonium acetate.

The amount of the quaternary ammonium compound is preferably 0.1 to 10 mmol, more preferably 0.2 to 5 mmol, and still more preferably 0.5 to 1 mmol, based on 1 g of the hydrogenation catalyst. The amount thereof is preferably 1 to 20 mass %, more preferably 3 to 10 mass %, and still more preferably 5 to 10 mass %, based on the hydrogenation catalyst. By using the quaternary ammonium compound in the above amount, the catalyst is not deteriorated, the reaction rate is maintained, and a desired aromatic aminomethyl can be obtained in a high yield. When the amount of the quaternary ammonium compound is 20 mass % or less based on the hydrogenation catalyst, the amount of water brought into can be suppressed even if the quaternary ammonium compound is used as an aqueous solution.

(Metal Hydroxide)

The metal hydroxide used in the present invention is at least one selected from the group consisting of an alkali metal hydroxide and an alkaline earth metal hydroxide, and in particular, an alkali metal hydroxide is preferable.

As the alkali metal hydroxide, preferable is one or more selected from the group consisting of sodium hydroxide and potassium hydroxide, and among these, more preferable is sodium hydroxide.

As the alkaline earth metal hydroxide, preferable is one or more selected from the group consisting of calcium hydroxide and magnesium hydroxide, and among these, more preferable is calcium hydroxide.

That is to say, as the metal hydroxide, preferable is one or more selected from the group consisting of sodium hydroxide, potassium hydroxide, calcium hydroxide and magnesium hydroxide, and among these, more preferable is one or more selected from the group consisting of sodium hydroxide, potassium hydroxide and calcium hydroxide, still more preferable is one or more selected from the group consisting of sodium hydroxide and potassium hydroxide, and still much more preferable is sodium hydroxide.

The amount of the metal hydroxide is preferably 0.1 to 10 mmol, more preferably 0.2 to 5 mmol, and still more preferably 0.5 to 1 mmol, based on 1 g of the hydrogenation catalyst. Moreover, the amount thereof is preferably 1 to 20 mass %, more preferably 3 to 10 mass %, and still more preferably 5 to 10 mass %, based on the hydrogenation catalyst. It is thought that by using the metal hydroxide in the above amount, impurities are also suppressed, the reaction rate is maintained, and a desired aromatic aminomethyl can be obtained in a high yield. Furthermore, when the amount of the metal hydroxide is 20 mass % or less based on the hydrogenation catalyst, the amount of water brought into can be suppressed even if the metal hydroxide is used as an aqueous solution.

The molar ratio of the quaternary ammonium compound to the metal hydroxide (quaternary ammonium compound/metal hydroxide) is preferably 70/30 to 20/80, more preferably 60/40 to 30/70, still more preferably 50/50 to 35/65, and still much more preferably 45/55 to 40/60. When the molar ratio is in this range, the aromatic aminomethyl can be obtained in a high yield, and in addition, the catalyst deterioration rate is low, repeated use of the catalyst is possible, and impurities can be sufficiently reduced, so that such a range is preferable.

(Hydrogenation Catalyst)

The hydrogenation catalyst used in the production method of the present invention is not restricted as long as it is a catalyst used for hydrogenation of an organic compound, but a metal catalyst is preferable. Examples of metals contained in the metal catalyst include cobalt, nickel, palladium and platinum, and preferable is one or more selected from the group consisting of cobalt and nickel, and more preferable is cobalt. That is to say, a metal catalyst containing one or more selected from the group consisting of cobalt, nickel, palladium and platinum is preferable, a metal catalyst containing one or more selected from the group consisting of nickel and cobalt is more preferable, and a metal catalyst containing cobalt is still more preferable. By using a cobalt catalyst, formation of a high-boiling substance on the catalyst is inhibited, the yield can be enhanced, and moreover, deterioration of the catalyst can also be reduced.

Examples of the metal catalysts containing one or more selected from the group consisting of nickel and cobalt include a metal-supported catalyst and a sponge metal catalyst, and preferable is a sponge metal catalyst.

Examples of the metal-supported catalysts include catalysts in which one or more selected from the group consisting of nickel and cobalt are supported on $Al_2O_3$, $SiO_2$, diatomaceous earth, $SiO_2$—$Al_2O_3$, or $ZrO_2$ by a precipitation method.

Examples of the sponge metal catalysts include catalysts formed by eluting part of components from an alloy of two or more components (nickel, cobalt, aluminum, iron, copper, etc.) using an acid or an alkali, and preferable are a sponge cobalt catalyst and a sponge nickel catalyst, and more preferable is a sponge cobalt catalyst. The above catalysts may be used singly or in combination of two or more.

The amount of the catalyst is preferably 0.1 to 100 parts by mass, more preferably 1 to 50 parts by mass, and still more preferably 10 to 20 parts by mass, based on 100 parts by mass of the aromatic nitrile. By using the catalyst in the above amount, the yield of the resulting aromatic aminomethyl can be enhanced.

(Aromatic Nitrile)

The aromatic nitrile used as a starting material in the production method of the present invention is one in which a nitrile group is bonded to an aromatic ring (benzene ring), and the number of nitrile groups is preferably 1 or 2, and more preferably 2.

To the aromatic ring, other substituents may be bonded.

Specific examples of the aromatic nitriles include benzonitrile and dicyanobenzene, and dicyanobenzene is preferably used.

The dicyanobenzene has three isomers of phthalonitrile (1,2-dicyanobenzene), isophthalonitrile (1,3-dicyanobenzene), and terephthalonitrile (1,4-dicyanobenzene), and preferable are isophthalonitrile and terephthalonitrile, and more preferable is terephthalonitrile.

The concentration of the aromatic nitrile in the reaction solution in the hydrogenation reaction is preferably 2 to 30 mass %, more preferably 5 to 25 mass %, and still more preferably 7 to 20 mass %. In the reaction solution, a catalyst is not contained. In the reaction solution, a starting material, an organic solvent, a liquid component other than the organic solvent, such as water, a quaternary ammonium compound, and a metal hydroxide are contained. The concentration of the aromatic nitrile during the hydrogenation reaction can be calculated as a concentration based on the total of masses of the components for constituting a homogeneous solution when the components are blended in the method for producing an aromatic aminomethyl described later. In other words, the concentration of the aromatic nitrile during the hydrogenation reaction can be calculated as a concentration based on the total of masses of the aromatic nitrile that is a starting material, the organic solvent used for the hydrogenation reaction, the liquid component other than the organic solvent, such as water, the quaternary ammonium compound, and the metal hydroxide in the blending of them.

(Aromatic Aminomethyl)

The aromatic aminomethyl obtained by the production method of the present invention is one in which an aminomethyl group is bonded to an aromatic ring (benzene ring), and the number of aminomethyl groups is preferably 1 or 2, and more preferably 2.

To the aromatic ring, other substituents may be bonded.

Specific examples of the aromatic aminomethyls include benzylamine and xylenediamine, and preferable is xylenediamine.

The xylenediamine has three isomers of ortho-xylenediamine, meta-xylenediamine and para-xylenediamine, and preferable are meta-xylenediamine and para-xylenediamine, and more preferable is para-xylenediamine.

These isomers of the xylenediamine can be each obtained by the production method of the present invention using the corresponding dicyanobenzene as a starting material.

(Method for Producing Aromatic Aminomethyl)

The method for producing an aromatic aminomethyl of the present invention comprises hydrogenating an aromatic nitrile in an organic solvent comprising a polar organic solvent having a solubility parameter (SP value) of 9 or more in the presence of a quaternary ammonium compound, at least one metal hydroxide selected from the group consisting of an alkali metal hydroxide and an alkaline earth metal hydroxide, and a hydrogenation catalyst.

In the present production method, the order of blending a starting material, etc. is not particularly restricted, but it is preferable to introduce the organic solvent, the quaternary ammonium compound, the metal hydroxide and the hydrogenation catalyst and then introduce hydrogen into a pressure container.

In order that a gas other than hydrogen, such as air, or water should not be introduced into the hydrogenation catalyst, the hydrogenation catalyst is preferably added as a slurry of the catalyst by immersing the catalyst in water and then replacing the water with the organic solvent.

For the reaction in the present production method, both of a batch process and a continuous process can be also carried out, but a batch process is preferable.

In the present invention, as hydrogen that is a starting material used in the hydrogenation, one having been purified does not need to be particularly used, and it may be an industrial-grade one. The hydrogen pressure in the reaction is preferably 2.0 to 20.0 MPa, more preferably 3.0 to 15.0 MPa, and still more preferably 5.0 to 10.0 MPa. When the hydrogen pressure is in the above range, the yield of a product is sufficient, a pressure container with high pressure becomes unnecessary, and the cost can be reduced, so that the above hydrogen pressure is preferable.

The reaction temperature is preferably 20 to 150° C., more preferably 50 to 130° C., and still more preferably 60 to 120° C. When the reaction temperature is in this range, a conversion ratio of the aromatic nitrile that is a starting material is good, and formation of a side product is inhibited, so that the yield is enhanced.

The reaction time varies depending on the reaction temperature, the hydrogen pressure, etc., but under the above conditions, the reaction time is usually set to 0.1 to 100 hours, and preferably 0.5 to 10 hours.

The resulting aromatic aminomethyl can be recovered using a known method. For example, the aromatic aminomethyl is preferably recovered by separating a gas component and a liquid component from a reaction mixture at the time of completion of the reaction, filtering out a solid component such as a catalyst, and then distilling the liquid component. It is also preferable to further distil the resulting aromatic aminomethyl to enhance purity.

EXAMPLES

The present invention will be specifically described based on the examples shown below, but the present invention is in no way restricted by these examples. In the following examples, a gas chromatograph was used for the composition analysis.

<Gas Chromatography (GC) Analysis Conditions>

The gas chromatography analysis was carried out under the following conditions.

Equipment used: Gas Chromatograph Nexis GC-2030 (manufactured by Shimadzu Corporation)

Column: DB-1 (length 30 m, inner diameter 0.53 mm, film thickness 1.5 μm)

Detector: FID ($H_2$ 30 mL/min, Air 300 mL/min)

Carrier gas: He (constant flow; average linear velocity 38 cm/sec)
Split ratio: 28.1
Injection port temperature: 300° C.
Detector temperature: 300° C.
Injection amount: 1.0 μL
Oven temperature: The temperature was raised from 50° C. up to 150° C. at 5° C./min, and after the temperature reached 150° C., the temperature was raised up to 280° C. at 10° C./min and then maintained for 7 minutes. Thereafter, the temperature was raised up to 300° C. at 10° C./min and maintained for 5 minutes.

<Conversion Ratio and Yield>

A conversion ratio of a starting material (terephthalonitrile) and a yield of a product (para-xylenediamine) were calculated from the amounts of the starting material and the product in a reaction mixture after the hydrogenation reaction obtained in each of the examples and the comparative example, the amounts having been measured by an internal standard method using the gas chromatography. In order to use diphenylmethane as an internal standard, a calibration curve was prepared in advance by using a solution of terephthalonitrile and para-xylenediamine of known concentrations.

A sample in which 0.5 g of diphenylmethane had been added to 5.0 g of a reaction mixture was prepared, the sample was subjected to gas chromatography measurement under the aforesaid conditions, and a conversion ratio and a yield were determined by the following equations.

Conversion ratio (mol %)=[1−(amount of terephthalonitrile in reaction mixture [mol])/(amount of terephthalonitrile in preparation [mol])]×100

Yield (mol %)=(amount of para-xylenediamine in reaction mixture [mol])/(amount of terephthalonitrile in preparation [mol])×100

<Impurity Concentration>

The impurity concentration was calculated from the amount of impurities based on the amount of the product after distillation obtained in each of the examples and the comparative example. Calculation of the impurity concentration was carried out by a simple area method using the gas chromatography.

The area of impurities was taken as the total of areas of peaks having the same retention times as those of 1-(4-(aminomethyl)phenyl)-N-methylmethaneamine and 1-(4-aminomethyl)phenyl)-N-ethylmethaneamine that were main components of impurities (total area of N-alkyl compounds), the area of the product was taken as an area of all peaks except a diluent solvent (area of product), and the impurity concentration was determined by the following equation.

Impurity concentration (%)=(total area of N-alkyl compounds)/(area of product)×100

Example 1

(Preparation of Catalyst Slurry)

The following operations were carried out using a 50 mL beaker. In 30 mL of water, 5.90 g of a Raney cobalt catalyst (sponge cobalt catalyst) (RANEY 2724, manufactured by W.R. Grace & Co.) was introduced, and they were allowed to stand still to settle down the catalyst, followed by removing a supernatant by decantation. Next, 30 mL of methanol was added, stirring was carried out for 1 minute, and then a supernatant was removed in the same manner as above. The above replacement with methanol was carried out five times, thereby preparing a methanol slurry of the catalyst.

(Hydrogenation Reaction)

In a 500 mL autoclave container, the methanol slurry of the catalyst (catalyst quantity 5.90 g) was introduced, and adjustment was made in such a manner that the total mass of methanol became 39.5 g. Subsequently, 51.8 g of terephthalonitrile, 197.3 g of m-xylene and 0.76 g of a 25% tetramethylammonium hydroxide aqueous solution (2.1 mmol, 0.19 g, as tetramethylammonium hydroxide, 0.084 g of sodium hydroxide (2.1 mmol)) were introduced.

Nitrogen purge of the reactor was carried out by a method including pressurizing the reactor up to 0.5 MPa with nitrogen and returning the pressure to atmospheric pressure. This nitrogen purge was carried out three times in total, and then using hydrogen, hydrogen purge was carried out three times in total in the same manner as above.

The hydrogen pressure was set at 8.0 MPa, and the temperature was raised up to 100° C. while stirring at 1200 rpm, and reaction was carried out under the conditions of 100° C. while feeding hydrogen to maintain the pressure at 8.0 MPa. When hydrogen was no longer consumed, the reaction was completed. After completion of the reaction, a reaction mixture was cooled down to 50° C. and then subjected to pressure filtration at a pressure of 0.4 MPa to filter out the catalyst, thereby obtaining a reaction mixture containing para-xylenediamine that was a reaction product. The same hydrogenation reaction was further carried out twice, and the reaction mixtures of reactions of three times were mixed and put together, thereby obtaining a reaction mixture to be used for distillation and measurement/calculation of a conversion ratio and a yield. Using the reaction mixture, the aforesaid conversion ratio and yield were determined.

(Distillation)

Using a glass jacket type distillation column (number of distillation plates: 10 plates), rectification of para-xylenediamine was carried out. A three-neck flask was charged with the reaction mixture. Distillation was carried out by being divided into four stages shown in the following (1) to (4). Using a product obtained after the distillation, the impurity concentration was determined.

(1) Pressure: 760 torr, reflux ratio: 5, bottom temperature: 74° C.→149° C., top temperature: start temperature 64° C.; when the top temperature reached 139° C., the distillation was completed.

(2) Pressure: 300 torr, reflux ratio: 1, bottom temperature: start temperature 115° C., top temperature: 108° C.; when the bottom temperature reached 170° C., the distillation was completed.

(3) Pressure: 10 torr, reflux ratio: 15, bottom temperature: 123° C.→142° C., top temperature: 139° C.; when 10 mass % of the initial reaction mixture was distilled away, the distillation was completed.

(4) Pressure: 10 torr, reflux ratio: 1, bottom temperature: start temperature 142° C., top temperature: 139° C.; when the bottom temperature reached 155° C., the distillation was completed.

Example 2

A reaction mixture was obtained by carrying out the same operations as in Example 1 to perform hydrogenation reactions of three times, except that 0.67 g of a 35% tetraethylammonium hydroxide aqueous solution (1.6 mmol, 0.19 g in terms of tetraethylammonium hydroxide) was used instead of the 25% tetramethylammonium hydroxide aqueous solution, and the amount of sodium hydroxide was changed to 0.096 g (2.4 mmol). Using the reaction mixture, the aforesaid conversion ratio and yield were determined. Moreover, using the reaction mixture, distillation was carried out by the same operations as in Example 1, thereby obtaining a product. Using the product obtained after the distillation, the aforesaid impurity concentration was determined.

Comparative Example 1

A reaction mixture was obtained by carrying out the same operations as in Example 1 to perform hydrogenation reactions of three times, except that sodium hydroxide was not used. Using the reaction mixture, the aforesaid conversion ratio and yield were determined. Moreover, using the reaction mixture, distillation was carried out by the same operations as in Example 1, thereby obtaining a product. Using the product obtained after the distillation, the aforesaid impurity concentration was determined.

TABLE 1

|  |  | Example 1 | Example 2 | Comparative Example 1 |
|---|---|---|---|---|
| Aromatic nitrile (starting material) | | Terephthalonitrile | Terephthalonitrile | Terephthalonitrile |
| Quaternary ammonium compound | | Tetramethylammonium hydroxide | Tetraethylammonium hydroxide | Tetramethylammonium hydroxide |
| Amount added (mmol) | | 2.1 | 1.6 | 2.1 |
| Hydroxide of alkali metal | | Sodium hydroxide | Sodium hydroxide | — |
| Amount added (mmol) | | 2.1 | 2.4 | — |
| Organic solvent | Polar organic solvent | Methanol | Methanol | Methanol |
|  | Hydrocarbon solvent | m-Xylene | m-Xylene | m-Xylene |
| Hydrogenation catalyst | | Raney cobalt | Raney cobalt | Raney cobalt |
| Aromatic aminomethyl (product) | | Para-xylenediamine | Para-xylenediamine | Para-xylenediamine |
| Evaluation of reaction mixture | Conversion ratio (mol %) | 100 | 100 | 100 |
|  | Yield (mol %) | 92.6 | 94.8 | 94.7 |
| Evaluation of product | Impurity concentration (%) | 0.10 | 0.01 | 0.17 |

From the results of Table 1, it has been found that when the production method of the examples is used, para-xylenediamine can be obtained in a high yield, and further, the impurity concentration in the product is also low, and formation of impurities can also be suppressed.

The invention claimed is:

1. A method for producing an aromatic aminomethyl, comprising hydrogenating an aromatic nitrile in an organic solvent comprising a polar organic solvent having a solubility parameter (SP value) of 9 or more in the presence of a quaternary ammonium compound, at least one metal hydroxide selected from the group consisting of an alkali metal hydroxide and an alkaline earth metal hydroxide, and a hydrogenation catalyst.

2. The method for producing an aromatic aminomethyl according to claim 1, wherein the quaternary ammonium compound is one or more selected from the group consisting of a tetraalkylammonium hydroxide and an organic acid tetraalkylammonium salt.

3. The method for producing an aromatic aminomethyl according to claim 1, wherein the metal hydroxide is one or more selected from the group consisting of sodium hydroxide and potassium hydroxide.

4. The method for producing an aromatic aminomethyl according to claim 1, wherein the organic solvent further comprises a hydrocarbon solvent.

5. The method for producing an aromatic aminomethyl according to claim 4, wherein a mass ratio of the hydrocarbon solvent to the polar organic solvent (hydrocarbon solvent/polar organic solvent) in the organic solvent is 60/40 to 99/1.

6. The method for producing an aromatic aminomethyl according to claim 4, wherein the total amount of the hydrocarbon solvent and the polar organic solvent in the organic solvent is 90 to 100 mass %.

7. The method for producing an aromatic aminomethyl according to claim 1, wherein the hydrogenation catalyst is a metal catalyst comprising one or more selected from the group consisting of nickel and cobalt.

8. The method for producing an aromatic aminomethyl according to claim 1, wherein the amount of the quaternary ammonium compound is 1 to 20 mass % based on the hydrogenation catalyst.

9. The method for producing an aromatic aminomethyl according to claim 1, wherein the amount of the metal hydroxide is 1 to 20 mass % based on the hydrogenation catalyst.

10. The method for producing an aromatic aminomethyl according to claim 1, wherein a molar ratio of the quaternary ammonium compound to the metal hydroxide (quaternary ammonium compound/metal hydroxide) is 70/30 to 20/80.

11. The method for producing an aromatic aminomethyl according to claim 4, wherein the hydrocarbon solvent is an aromatic hydrocarbon solvent.

12. The method for producing an aromatic aminomethyl according to claim 1, wherein the polar organic solvent is an alcohol.

13. The method for producing an aromatic aminomethyl according to claim 1, wherein the organic solvent does not comprise liquid ammonia.

14. The method for producing an aromatic aminomethyl according to claim 1, wherein a content of water in the organic solvent is 5 mass % or less.

15. The method for producing an aromatic aminomethyl according to claim 1, wherein the aromatic nitrile is dicyanobenzene.

16. The method for producing an aromatic aminomethyl according to claim 1, wherein the aromatic nitrile is terephthalonitrile.

17. The method for producing an aromatic aminomethyl according to claim 1, wherein the aromatic aminomethyl is xylenediamine.

18. The method for producing an aromatic aminomethyl according to claim 4, wherein the aromatic aminomethyl is xylenediamine.

\* \* \* \* \*